United States Patent [19]
Martinez et al.

[11] Patent Number: 4,636,490
[45] Date of Patent: Jan. 13, 1987

[54] NOVEL PEPTIDIC DERIVATIVES INHIBITING GASTRIC SECRETION, PROCESS FOR PREPARING THEM AND DRUGS CONTAINING THEM

[75] Inventors: Jean Martinez, Caux; Jean-Pierre Bali, Saint-Gely du Fesc; Bertrand Castro, Perols, all of France; Dino Nisato, Pavia, Italy; Henri Demarne, Montpellier, France

[73] Assignees: Sanofi; Centre National de la Recherche Scientifique, both of Paris, France

[21] Appl. No.: 597,427

[22] Filed: Apr. 6, 1984

[30] Foreign Application Priority Data

Apr. 20, 1983 [FR] France ................. 83 06492

[51] Int. Cl.$^4$ .................... A61K 37/43; C07K 7/06
[52] U.S. Cl. ..................... 514/15; 514/16; 514/17; 530/328; 530/329; 530/330
[58] Field of Search ........... 260/112.5 R; 514/15, 514/16, 17; 530/328, 329, 330

[56] References Cited

U.S. PATENT DOCUMENTS 3,896,103 7/1975 Hardy et al. ................. 260/112.5 R
4,351,829 9/1982 Zetler et al. ................. 260/112.5 R

FOREIGN PATENT DOCUMENTS 0124420 11/1984 European Pat. Off. .

OTHER PUBLICATIONS

Chemical Abstracts, 101, 86 (1984), Abst. No. 222854z.
FR-M- 5 336 (ICI)* Resume I * 1,7.
Unlisted Drugs, 1974, Special Libr. Assoc., *p. 86b: "CTO"*, 1,7.

Primary Examiner—Delbert R. Phillips
Attorney, Agent, or Firm—Bacon & Thomas

[57] ABSTRACT

The invention relates to peptides of general formula:

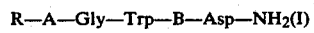

in which:
Asp $NH_2$ represents the amide in $\alpha$ position of the aspartic acid of formula:

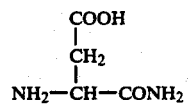

R represents hydrogen, a protector group of the terminal amine function such as t.butyloxy carbonyl (BOC), benzyloxy carbonyl (Z), lower alkanoyl,
A designates:
either tyrosine, tyrosine-O-sulfate, threonine or methionine;
or a dipeptide selected from: —Ala—TYR—, —TYR—Thr—, —TYR Met—, TYR designating either of the 2 amino-acids tyrosine or tyrosine-O-sulfate;
or a tripeptide selected from: —Glu—Ala—TYR—, Asp—TYR—Thr—, —Asp—TYR—MET—;
or a tetrapeptide selected from: —Glu—Glu—Ala—TYR—, —Gln Asp—TYR—Thr—, —Arg—ASP—TYR—Met—;
or a pentapeptide selected from: —Glu—Glu—Glu—Ala—TYR—, —Pyr—Gln—Asp—TYR—Thr—, —Asp—Arg—Asp—TYR—Met;
B designates methionine, leucine or norleucine.

15 Claims, No Drawings

NOVEL PEPTIDIC DERIVATIVES INHIBITING GASTRIC SECRETION, PROCESS FOR PREPARING THEM AND DRUGS CONTAINING THEM

The present invention relates to novel peptidic derivatives inhibiting gastric secretion and to a process for preparing them.

Caerulein, cholecystokinin and gastrin are natural polypeptides endowed with various pharmacological activities.

For example, gastrin stimulates gastric secretion, cholecystokinin stimulates the release of pancreatic enzymes, whilst caerulein increases gastric, pancreatic and biliary secretions.

From the structural standpoint, these three compounds present the same C-terminal sequence which, using the 3-letter abbreviations recommended by the Commission of Nomenclature of the IUPAC-IUB for designating the α-aminoacids, may be represented by:

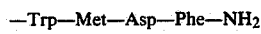

—Trp—Met—Asp—Phe—NH₂

According to the present invention, it has been found that peptidic compounds derived from the C-terminal sequences of caerulein, cholecystokinin and gastrin by elimination of the terminal Phe NH₂ group unexpectedly possess the property of inhibiting gastric secretion.

These compound correspond to the general formula where all the aminoacids are of L configuration:

R—A—Gly—Trp—B—Asp—NH₂ (I)

in which:

Asp NH₂ represents the amine in α position of the aspartic acid of formula:

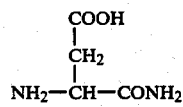

```
        COOH
         |
         CH₂
         |
NH₂—CH—CONH₂
```

R represents hydrogen, a protector group of the terminal amine function such as t.butyloxy carbonyl (BOC), benzyloxy carbonyl (Z), lower alkanoyl, etc.

A designates:
either tryosine, tryosine-O-sulfate, threonine or methionine;
or a dipeptide selected from: —Ala—TYR—, —TYR—Thr—, —TYR—Met—, TYR designating either of the 2 amino-acids tyrosine or tyrosine-O-sulfate;
or a tripeptide selected from: —Glu—Ala— TYR—, Asp—TYR—Thr—, —Asp—TYR—Met—;
or a tetrapeptide selected from: —Glu— Glu—Ala—TYR—, —Gln—Asp—TYR—Thr—, —Arg—Asp—TYR—Met—;
or a pentapeptide selected from: —Glu—Glu—Glu—Ala—TYR—, —Pyr—Gln—Asp—TYR—Thr—, —Asp—Arg—Asp—TYR—Met—;

B designates methionine, leucine or norleucine.

The compounds according to the invention may be prepared by the conventional techniques of peptidic synthesis either in solid phase according to Merrifield, or in liquid phase.

From the α-amide aspartic acid, the different aminoacids present in the sequence are successively introduced. The reactions of coupling are carried out with an activated ester of the amino acid to be introduced within dimethylformamide and in the presence of diisopropylethylamine and 1-hydroxy benzotriazole.

All the aminoacids are incorporated in the form of the protected derivative of the amine in α position, the protector group being selected from the benzyloxycarbonyl and t-butyloxycarbonyl groups. When the aminoacid used presents in its side chain functions capable of reacting, the latter must be previously blocked. Thus the acid functions in ε position of the aspartic acid or of the glutamic acid must be blocked in the form of ester in particular benzyl ester or tertiobutyl ester and the guanidino group of arginine may be protected by a nitro group.

After each reaction of coupling, deprotection of the amine in α position is effected either by hydrogenolysis if it is a benzyloxy carbonyl group, or by acid hydrolysis if it is a butyloxycarbonyl group.

Finally, the peptides protected in their functions of the side chains are partially or entirely deprotected in order to lead to the compounds of formula (I).

The compounds of formula (I), where TYR represents tyrosine-O-sulfate, are obtained from the compounds where TYR represents tyrosine by action sulfuric anhydride in the presence of pyridine.

The following non-limiting Examples enable the invention to be more readily understood.

In these Example, the following abbreviations will be used:

Amino acids and protector groups

| | |
|---|---|
| Ala | Alanine |
| Asp NH₂ | α-amide aspartic acid |
| Met | Methionine |
| Trp | Tryptophane |
| Glu | Glutamic acid |
| Gly | Glycine |
| Tyr | Tyrosine |
| Tyr(HSO₃) | Tyrosine-O—sulfate |
| Pyr | Pyroglutamic acid |

With the exception of glycine, all these amino acids are of L configuration.

| | |
|---|---|
| Boc | Tertiobutyloxycarbonyl |
| Z | Benzyloxycarbonyl |
| Bzl | Benzyl |
| O buᵗ | O—tertiobutyl |
| CAM | carboxamidomethyl |
| FMOC | fluorenyl-methyl-oxycarbonyl |
| ONSu | (succinimidyl-oxy group) |
| ONp | (p-nitrophenoxy group) |

The following abbreviations will also be used:

| | |
|---|---|
| DIEA | Diisopropylethylamine |

| HOBt | 1-hydroxy benzotriazole |
| BOP | hexafluorophosphate of benzotriazolyloxy tris dimethylaminophosphonium |

EXAMPLE 1

H—Met—Gly—Trp—Met—Asp NH$_2$ (I) R=H; A=Met; B=Met (a) —Z—Asp($\beta$OBu$^t$)—NH$_2$ 5 g of N-benzyloxycarbonyl aspartic α ester acid of tertiobutyl N-hydroxy succinimide β ester are dissolved in a mixture of 100 ml of ethyl acetate and 100 ml of dichloromethane. A stream of gaseous ammonia is passed above the solution which is stirred well for 1 hour.

The expected product is obtained by evaporation.

m.p.: 88°-92°; yield: 95%.

(b) —Z—Met—Asp($\beta$OBu$^t$)—NH$_2$

The solution of 3.5 g of the compound obtained under (a) in absolute ethanol has 2 ml of hydrochloric acid and 0.35 g of palladium over 10% charcoal added thereto. It is hydrogenated for 4 hours then the catalyst is filtered and the solvent is evaporated. The residue is washed several times with ether, then it is added to a solution of 2.7 g of Z—Met—ONp, 2.3 ml of DIEA and 0.9 g of HOBt in dimethylformamide.

After 24 hours, the solvent is evaporated in vacuo and the residue is taken up in dichloromethane. The solution is washed with water several times with a 5% hydrochloric acid solution and with a solution saturated with sodium bicarbonate. The product is evaporated to dryness in vacuo and the expected product is obtained.

m.p.: 155°-157° C.; yield: 80%.

$[\alpha]_D^{25} = -3.9$ (c=1, dimethylformamide)

(c) —Z—Trp—Met—Asp($\beta$OBu$^t$)—NH$_2$ 2.2 g of the compound obtained above are dissolved in a mixture of 150 ml of dimethylformamide, 30 ml of water and 15 ml of DIEA. 0.4 g of palladium over 10% barium sulfate is added and the mixture is hydrogenated overnight.

The catalyst is filtered, and the solvents are concentrated in vacuo. The residue is dissolved in dimethylformamide (100 ml) and 1.8 g of Z—Trp—ONp, 1.6 g of DIEA and 0.75 g of HOBt are added.

The products are left overnight in contact then concentrated to about 50 ml and filtered over 30 g of neutral alumina. Elution continues with 200 ml of dimethylformamide, the product is evaporated to dryness and the residue is triturated with ethyl acetate.

A white powder is obtained.

$[\alpha]_D^{25} = -30$ (c=1, dimethylformamide); yield: 82%.

(d) —Z—Gly—Trp—Met—Asp($\beta$OBu$^t$)—NH$_2$

Using the compound obtained hereinabove, operation is carried out as indicated in paragraph (c), replacing Z—Trp—ONp by an equivalent quantity of Z—Gly—ONp.

A white powder is obtained in the same manner.

m.p.: 187°-189° C.; yield: 75%.

$[\alpha]_D^{25} = -18$ (c=1, dimethylformamide)

(e) —Boc—Met—Gly—Trp—Met—Asp($\beta$OBu$^t$)—NH$_2$

Using the compound obtained in paragraph (d), operation is carried out as indicated in paragraph (c), replacing Z—Trp—ONp by an equivalent quantity of Boc—Met—ONp. The expected product is isolated in the same manner.

m.p.: 194° C. (dec); yield: 75%.

(f) —H—Met—gly—Trp—Met—Asp—NH$_2$

The protected peptide obtained hereinabove is dissolved in trifluoroacetic acid in a proportion of 5 ml per g of product and 0.5 ml of anisole and 0.5 ml of thioanisole are added. The products are left in contact for 2 hours then 200 ml of ether are added. The precipitate is drained and washed several times with ether.

Trifluoroacetate in the form of a colourless solid is obtained.

Yield: 85%.

EXAMPLE 2

Z—Tyr—Met—Gly—Trp—Met—Asp—NH$_2$ (I) R=Z; A= —Tyr—Met; B=Met 1.8 g of the trifluoroacetate obtained in Example 1(f) are dissolved in dimethylformamide, then 1.12 g of Z—Tyr—ONp and 0.71 g of DIEA are added and left for 12 hours in contact.

Ethyl acetate is added and the precipitate is drained and washed several times with ethyl acetate then with ether.

The product is chromatographed over silica gel and, by eluting with the (60-20-6-10 vol/vol) ethyl acetate-pyridine-acetate acid-water mixture, the expected product is obtained with a yield of 80%.

EXAMPLE 3

Z—Tyr(HSO$_3$)—Met—Gly—Trp—Met—Asp—NH$_2$ (I) R=Z; A= —Tyr(HSO$_3$)—Met; B=Met 0.1 g of the peptide obtained in Example 2 is dissolved in 3 ml of dimethylformamide and 3 ml of pyridine. 0.75 g of the sulfuric anhydride/pyridine complex is added and the mixture is stirred overnight.

The solvents are evaporated in vacuo and the pH is taken to 6.5-7 by the addition of sodium bicarbonate saturated solution. The product is left for 1 hour in contact then the precipitate is isolated and purified by chromatography over silica gel in a manner similar to the purification of the peptide of Example 2.

The expected product is obtained with a yield of 55%.

m.p. 260° C. (dec).

IR spectrum: a band at 1060 cm$^{-1}$ due to the sulfate.

Rf=0.3 (ethyl acetate 60-pyridine 20-acetic acid 6-water 10, vol/vol).

EXAMPLE 4

Boc—Tyr—Gly—Trp—Met—Asp—NH$_2$ (I) R=Boc; A=Tyr; B=Met (a) —Boc—Met—Asp($\beta$OBzl)—NH$_2$ 1.91 g of trifluoroacetate of Asp($\beta$OBzl)—NH$_2$ are dissolved in 10 ml of dimethylformamide and 2.07 g of Boc—Met—ONp and 0.76 g of HOBt are added.

The solution is cooled to 5° C. and 2.06 ml of DIEA are added. After 8 hours, the mixture is concentrated in vacuo and the oily residue is taken up in ethyl acetate (200 ml). The organic solution is washed with a sodium bicarbonate saturated solution (twice 50 ml), with water (once 50 ml), with a sodium chloride saturated solution (once 50 ml), with a 20% citric acid solution (once 50 ml) then again with water (once 50 ml) and with a sodium chloride saturated solution (once 50 ml). The organic solution is dried over sodium sulfate and the solvent is concentrated in vacuo at a temperature lower than 50° C.

The residue, washed several times with the (1-9, vol/vol) ethyl acetate-ether mixture, then with ether, crystallizes.

m.p.: 109°–111° C.; yield: 85%

Thin layer chromatography

Rf=0.4 (chloroform 7-hexane 3, vol/vol)
Rf=0.3 (ethyl acetate 8-hexane 2, vol/vol)

(b) —Boc—Trp—Met—Asp($\beta$OBzl)—NH$_2$ 2 g of the compound obtained hereinabove are dissolved in 5 ml of trifluoroacetic acid. The product is left for ½ hour then 100 ml of ether are added, with stirring. The precipitate which forms is drained, rinsed several times with ether then dried over potassium hydroxide.

The product is dissolved in 10 ml of dimethylformamide and 1.7 g of Boc—Trp—ONp and 0.56 g of HOBt are added. After having cooled to 5° C., 1.47 ml of DIEA are added.

The product is left for 8 hours and treated as indicated under (a). A solid is obtained, m.p.: 178°–180° C.; yield: 86%.

Thin layer chromatography

Rf=0.35 (chloroform 7-hexane 3, vol/vol)
Rf=0.2 (ethyl acetate 8-hexane 2, vol/vol).

(c) —Boc—Gly—Trp—Met—Asp($\beta$OBzl)—NH$_2$

The terminal Boc group of the peptide obtained in paragraph (b) is eliminated by action of the trifluoroacetic acid. 1 g of the trifluoroacetate obtained is dissolved in dimethylformamide and 0.48 g of Boc—Gly—ONp, 0.22 g of HOBt and 0.6 g of DIEA are added. After 8 hours of reaction, the solution is concentrated and treated as described in paragraph (a).

After evaporation of the solvent, a solid is obtained, m.p. 152°–156° C.; yield: 86%.

Thin layer chromatography 1 single spot of Rf=0.55 (ethyl acetate-methanol, 9-1 vol/vol)

(d) —Boc—Tyr—Gly—Trp—Met—Asp($\beta$OBzl)—NH$_2$

The product obtained in paragraph (c) (0.71 g) is treated with 3.5 ml of trifluoroacetic acid for 30 minutes at ambient temperature. By addition of ether, a white powder is precipitated which is drained, washed with ether and dried in vacuo in the presence of potassium hydroxide.

This solid is dissolved in dimethylformamide (10 ml) and 0.4 g of Boc—Tyr—ONp and 0.18 ml of DIEA are added. After 8 hours of reaction, the product is treated as indicated in paragraph (c). It is chromatographed over a column of silica gel, eluting with a 9-1 (vol/vol) ethyl acetate-methanol mixture, to obtain a solid, m.p.: 128°–135° C.; yield: 72%.

Thin layer chromatography 1 single spot of Rf=0.4 (ethyl acetate-methanol, 95-5, vol/vol)

(e) —Boc—Tyr—Gly—Trp—Met—Asp—NH$_2$ 0.2 g of the product obtained hereinabove is dissolved in an (8-1-1, vol/vol) dimethylformamide-water-DIEA mixture and the product is hydrogenated in the presence of palladium over 10% barium sulfate (0.050 g) for 12 hours. The catalyst is filtered and the solvents are evaporated to dryness in vacuo at a temperature lower than 50° C.

The residue is taken up in 20 ml of ethyl acetate and 20 ml of 5% ammonium solution. The product is stirred and decanted. The aqueous phase is acidified by addition of solid citric acid and extracted twice with ethyl acetate. The organic extracts collected together are washed with water, dried and concentrated to dryness in vacuo. A white powder is obtained, m.p.: 210° C. (dec); yield: 56%.

Thin layer chromatography

Rf=0.4 (ethyl acetate 9-methanol 1-acetic acid 0.5, vol/vol).

EXAMPLE 5

Z—Glu—Ala—Tyr—Gly—Trp—Met—Asp—NH$_2$

R=Z; A=Glu—Ala—Tyr; B=Met (A)—Z—Glu($\gamma$OBut)—Ala—Tyr—Gly—OH (a) —Boc—Gly—Cam This product is prepared in accordance with the method of GISIN by action of alpha chloroacetamide on Boc—glycine within dimethylformamide at 40°–50° C. for 24 hours.

Yield: about 80%; m.p.: 64°–67° C. (ether)

(b) —Boc—Tyr—Gly—Cam 2.4 g of Boc—Gly—Cam are dissolved in 10 ml of trifluoroacetic acid and left for 30 minutes. 150 ml of ether are added, the precipitate is drained, washed with ether several times and dried.

This product is dissolved in 20 ml of dimethylformamide and 3.22 g of Boc—Tyr—ONp are added. The product is cooled to 0° C. and 1.3 ml of DIEA is added. The product is left for 12 hours at ambient temperature then evaporated to dryness in vacuo, maintaining the temperature lower than 50° C. The residue is taken up in 200 ml of ethyl acetate, washed with a sodium bicarbonate solution, then with water, with a 10% citric acid solution and again with water.

The product is dried over sodium sulfate and evaporated to dryness in vacuo. A solid is obtained.

m.p. 113°–116° C. [$\alpha$]$_D^{20}$= −9.2 (C=1, dimethylformamide)

Yield: 85%

(c) —Boc—Ala—Tyr—Gly—Cam

The solution of 3.55 g of the dipeptide obtained hereinabove in 15 ml of trifluoroacetic acid is left for ½ hr. at ambient temperature. 200 ml of ether are added and the precipitate is drained and washed several times with ether and dried.

The solid is dissolved in 15 ml of dimethylformamide and 2.63 g of Boc—Ala—ONp and 1.7 ml of DIEA are added. After 12 hours at ambient temperature, the reaction mixture is treated as indicated in paragraph (b).

The expected product is isolated; m.p.: 129°–132° C. [$\alpha$]$_C^{20}$= −21.1 (C=1, dimethylformamide)

Yield: 80%

(d) —Z—Glu($\gamma$OBut)—Ala—Tyr—Gly—Cam 0.932 g of the tripeptide prepared hereinabove is treated with 5 ml of trifluoroacetic acid for 30 minutes at ambient temperature and the tripeptide deprotected with nitrogen is isolated by precipitation with ether as indicated previously. The product obtained is dissolved in 10 ml of dimethylformamide and 1.08 g of Z—Glu($\gamma$OBut)—ONp and 0.38 ml of DIEA are added. The product is left for 12 hours and treated as indicated previously.

m.p.: 135°–137° C. (1-1, vol/vol ethyl acetate-ether)
$[\alpha]_D^{20} = -12$ (C=1, dimethylformamide)
Yield: 85%

(e) —Z—Glu($\alpha$OBut)—Ala—Tyr—Gly—OH

To the solution of 1.37 g of the peptide prepared hereinabove in 25 ml of dimethylformamide is added, with stirring, the solution of 0.318 g of sodium carbonate in 25 ml of water then the product is left for 1 hr. 30 mins. with stirring.

The product is neutralized to a pH close to 7 by addition of a 20% citric acid solution and concentrated to dryness in vacuo. The residue is dissolved in 20 ml of a 20% sodium carbonate solution and the aqueous phase is washed twice with 15 ml of ethyl acetate. The aqueous phase is acidified, cold, by addition of solid citric acid. The precipitate is drained, washed with water and dried.

m.p.: 128°–135° C. $[\alpha]_D^{20} = -12$ (C=1, dimethylformamide)
Yield: 75%

(B) —FMOC—Trp—Met—Asp($\beta$OBut)—NH$_2$ (a) —FMOC—Met—Asp($\beta$OBut)NH$_2$ 5 g of Hcl, Asp($\beta$OBut)—NH$_2$, 7.42 g of FMOC methionine, 8.84 g of BOP are dissolved, cold, in 50 ml of dimethylformamide.

7.8 ml of DIEA are added and the product is stirred for 12 hours at ambient temperature, then it is evaporated to dryness in vacuo at a temperature lower than 50° C. The residue is taken up in a mixture of ethyl acetate-ether and left to crystallize.

m.p.: 184°–185° C. $[\alpha]_D^{20} = -9.1$ (C=1, dimethylformamide)
Yield: 87%

(b) —FMOC—Trp—Met—Asp($\beta$OBut)—NH$_2$ 5.41 g of the protected dipeptide obtained hereinabove are dissolved in 150 ml of dimethylformamide containing 15 ml of diethylamine and the product is left for 2 hours with stirring at ambient temperature.

The product is evaporated to dryness in vacuo and the residue is taken up in 20 ml of dimethylformamide. This solution is added to a solution containing 3.82 g of FMOC—Trp, 3.98 g of BOP and 3.4 ml of DIEA in 20 ml of dimethylformamide. The product is stirred for 12 hours at ambient temperature and treated as indicated in the preceding paragraph, crystallizing in ethyl acetate.

m.p.: 175° C. (decomposition) $[\alpha]_D^{20} = -23$ (C=1, dimethylformamide)
Yield: 75%

(C)
—Z—Glu—Ala—Tyr—Gly—Trp—Met—Asp—NH$_2$ (a) —Z—Glu($\gamma$OBut)—Ala—Tyr—Gly—Trp—Met—Asp($\beta$OBut)—NH$_2$ 5 g of the protected tripeptide of Example 5(B)-(b) are dissolved in 100 ml of dimethylformamide containing 10 ml of diethylamine and the product is left for 2 hours with stirring at ambient temperature. It is evaporated to dryness and the residue is taken up in 20 ml of dimethylformamide. 1.26 g of the protected tetrapeptide obtained in Example 5(A)-(e), 0.84 g of BOP and 0.69 ml of DIEA are added, and the product is stirred for 12 hours at ambient temperature. It is evaporated to dryness in vacuo and the residue is triturated in ethyl acetate. The product is filtered and washed with a sodium carbonate saturated solution, with water, with a 20% citric acid solution, with water and finally with ethyl acetate. It is dried in vacuo.

m.p.: 210° C. (decomposition)
$[\alpha]_D^{20} = -23$ (C=1, dimethylformamide)
Yield: 72%

(b)-Deprotection 1.1 g of the protected heptapeptide obtained hereinabove are dissolved in 10 ml of trifluoroacetic acid containing 1 ml of thioanisole. The product is left for 1 hour at ambient temperature then 200 ml of ether are added. The white solid which separates is drained and washed several times with ether then dried in vacuo.

m.p.: 210° C. (decomposition)
$[\alpha]_D^{20} = -24$ (C=1, dimethylformamide)
Yield: 97%

Pharmacological tests

The compounds according to the invention were studied as far as their therapeutical properties are concerned. More particularly, these compounds were studied in vivo as far as their gastric secretory effect in the rat is concerned.

The model chosen for measuring the secretory effect is that of the stomach of a reperfused, anaesthetized rat. The protocol followed is a modification of the one described previously by Ghosh and Schild.

A male rat of Wistar strain, weighing 300 g, having fasted for 18 hours, is anaesthetized with urethane (10% solution, 1.5 ml/100 g i.p.). A tracheotomy is then made, as well as a catheterism of the vein of the penis which will allow i.v. administration of the peptides. A cannula is then placed in the oesophagus up to the cardiac orifice and a second cannula in the duodenum (by a duodenotomy made about 3 cm from the pylorus) up to the antral gastric zone.

A propionic-succinic solute (pH 5.5) which gives a linear variation of the pH as a function of the concentration of H+ ions is used for perfusing the stomach in open or closed circuit with a flow rate of 3 ml/min. The body temperature, as well as that of the solute, is monitored and maintained at 30° C. The acid secretion of the stomach will bring about a variation in pH detected by the glass half-cell and recorded as a function of time. After stabilization of the basal secretion, gastrin is injected by the intravenous route, either in perfusion or in a single injection. The response is recorded as a function of time and the quantity of acid secretion is measured on the recording by difference with the basal secretion.

The same experiment is carried out either by injecting the peptide to be studied i.v. on a plateau of acid secretion stimulated by the gastrin, or by associating the peptide with the stimulant in variable ratios of concentration. Finally, the peptide is administered alone at different doses in order to examine its agonist effect.

The experiments carried out with the products of Example 3: Z—Tyr(HSO$_3$)—Met—Gly—Trp—Met—Asp—NH$_2$ and of Example 4: Boc—Tyr—Gly—Trp—Met—Asp—NH$_2$ have given the following results.

| | (A) Agonist effect | |
|---|---|---|
| Peptide | Dose | Secretary effect (40 mins.) |
| Example 3 | 1000 µg/kg | 0.15 µmol H+ |
| Example 4 | 5000 µg/kg | 0.1 µmol H+ |
| Example 5 | 10000 µg/kg | 0 |
| Gastrin (HG 13) | 0.5 µg/kg | 16 µmol H+ |

-continued

| | (B) Antagonist effect | | |
|---|---|---|---|
| Peptide | Dose of agonist (minigastrin) | Dose of antagonist | Inhibiting effect (%) |
| Example 3 | 1.5 μg/kg/hr (perfusion) | 1.5 mg/kg | 47.4 |
| | 0.6 μg/kg (single) | 1.5 mg/kg | 47 |
| Example 4 | 0.6 μg/kg (single) | 1.2 mg/kg | 50.4 |
| Example 5 | 0.6 μg/kg (single) | 1.5 mg/kg | 50 |

The results call for the following observations:
the compounds according to the invention have an agonist effect which is extremely weak vis-á-vis gastrin, and this despite the high value of the doses used;
the compounds according to the invention present a considerable inhibiting effect on the gastric secretion, of the order of 50% under the experimental conditions employed.

Consequently, the compounds according to the invention may be used in human therapeutics whenever it is expedient to reduce gastric secretion and in particular for the treatment of peptic ulcers.

The compounds of the present invention may preferably be administered by the injectable route: intravenous, intramuscular or sub-cutaneous. They are used in a solvent such as saline isotonic solution.

Dosage may vary depending on the intensity of the therapeutic effect desired, the seriousness of the disorder to be treated and the route of administration employed. It must therefore be determined for each patient as a function of these various criteria. It is most often included between 1 and 100 mg of active ingredient per kg of body weight.

What is claimed is:

1. Peptides of general formula:

R—A—Gly—Trp—B—Asp—NH₂    (I)

in which:
Asp NH₂ represents the amide in α position of the aspartic acid of formula:

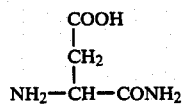

R represents hydrogen, a protector group of the terminal amine function which is t.butyloxy carbonyl (BOC), benzyloxy carbonyl (Z), or lower alkanoyl,
A designates:
  either tyrosine, tyrosine-O-sulfate, threonine or methionine;
  or a dipeptide selected from: —Ala—TYR—, —TYR—Thr—, —TYR Met—, TYR designates tyrosine or tyrosine-O-sulfate;
  or a tripeptide selected from: —Glu—Ala—TYR—, Asp—TYR—Thr—, —Asp—TYR—Met—;
  or a tetrapeptide selected from: —Glu—Glu—Ala—TYR—, —Gln—Asp—TYR—Thr—, —Arg—Asp—TYR—Met—;
  or a pentapeptide selected from: —Glu—Glu—Glu—Ala—TYR—, —Pyr—Gln—Asp—TYR—Thr—, —Asp—Arg—Asp—TYR—Met—;
B designates methionine, leucine or norleucine.

2. A peptide of claim 1 of formula

H—Met—Gly—Trp—Met—Asp—NH₂.

3. A peptide of claim 1 of formula:

R—Tyr—Met—Gly—Trp—Met—Asp—NH₂.

4. A peptide of claim 1 of formula :

R—Tyr(HSO₃)—Met—Gly—Trp—Met—Asp—NH₂.

5. A peptide of claim 1 of formula:

R—Tyr—Gly—Trp—Met—Asp—NH₂.

6. A peptide of claim 1 of formula:

Z—Glu—Ala—Tyr—Gly—Trp—Met—Asp—NH₂.

7. A process for preparing the peptides of claim 1, comprising the steps of:
  using α-amide aspartic acid as starting product,
  successively effecting on said acid the couplings of the various amino acids by using an activated ester of said acids, the reaction being carried out within dimethylformamide and in the presence of a compound selected from diisopropylethylamine and 1-hydroxy benzotriazole, said amino acids having been previously appropriately protected on their amine function in α position.

8. A peptide as claimed in claim 1, wherein A is tyrosine, tyrosine-O-sulfate, threonine or methionine.

9. A peptide as claimed in claim 1, wherein A is a dipeptide which is —Ala—TYR—, —TYR—Thr—, or —TYR—Met—.

10. A peptide as claimed in claim 1 wherein A is a tripeptide which is —Glu—Ala—TYR—, —Asp—TYR—Thr—, or —Asp—TYR—Met—.

11. A peptide as claimed in claim 1, wherein A is a tetrapeptide which is —Glu—Glu—Ala—TYR—, —Gln—Asp—TYR—Thr—, or —Arg—Asp—Tyr—Met—.

12. A peptide as claimed in claim 1, wherein A is a pentapeptide which is —Glu—Glu—Glu—Ala—TYR—, —Pyr—Gln—Asp—TYR—Thr—, or —Asp—Arg—Asp—Tyr—Met—.

13. A pharmaceutical composition for inhibiting gastric secretion which comprises a gastric secreting inhibiting amount of at least one peptide as claimed in claim 1, in association with a pharmaceutically acceptable carrier or diluent.

14. A composition as claimed in claim 13, wherein the peptide has the formula: R—Tyr—Gly—Trp—Met—Asp—NH₂.

15. A composition as claimed in claim 14 wherein R is BOC.

* * * * *